(12) United States Patent
Chang et al.

(10) Patent No.: US 6,646,259 B2
(45) Date of Patent: Nov. 11, 2003

(54) METHOD OF SAMPLE PREPARATION FOR TRANSMISSION ELECTRON MICROSCOPE ANALYSIS

(75) Inventors: Wen-Tung Chang, Hsin-Chu (TW); Hsing-Shuang Chou, Chu-Pei (TW); Jing-Fang Chiu, Hsin-Chu (TW)

(73) Assignee: United Microelectronics Corp., Hsin-Chu (TW)

( * ) Notice: Subject to any disclaimer, the term of this patent is extended or adjusted under 35 U.S.C. 154(b) by 327 days.

(21) Appl. No.: 09/813,050

(22) Filed: Mar. 20, 2001

(65) Prior Publication Data

US 2002/0134938 A1 Sep. 26, 2002

(51) Int. Cl.[7] .................................................. G01N 1/32
(52) U.S. Cl. .................... 250/307; 250/311; 250/492.21
(58) Field of Search ................................. 250/307, 309, 250/311, 492.21

(56) References Cited

U.S. PATENT DOCUMENTS 6,252,227 B1 * 6/2001 Tseng et al. ................ 250/307

* cited by examiner

*Primary Examiner*—Kiet Tuan Nguyen
(74) *Attorney, Agent, or Firm*—Dickinson Wright PLLC

(57) ABSTRACT

A method of sample preparation for transmission electron microscope analysis is disclosed. The method renders a typical TEM analysis on a sample having a photoresist layer practical. The method uses a conductive layer and a dielectric layer to protect a photoresist layer of the TEM sample from slicing damage and ion bombardment. The conductive layer and the dielectric layer can also isolate the photoresist layer from moisture and oxygen containing environments and prevent the photoresist layer from shrinking. Moreover, the entire TEM sample preparation process need not use any organic solvent or water to clean the sample.

35 Claims, 3 Drawing Sheets

METHOD OF SAMPLE PREPARATION FOR TRANSMISSION ELECTRON MICROSCOPE ANALYSIS

BACKGROUND OF THE INVENTION

1. Field of the Invention

The present invention relates to a method of sample preparation for transmission electron microscope analysis, and more particularly to a method of photoresist sample preparation for transmission electron microscope analysis.

2. Description of the Related Art

In the analysis of an ultra large scale integrated (ULSI) circuit, the profile images of an ULSI circuit sample are crucial. Particularly, as the dimension or the line width of the ULSI circuit advances to a scale under 0.2 micron, the profile images showing direct and strong evidence of various process results are the keys of further process technology development and the bases of solving various processing problem resulting device failures. A scanning electron microscope (SEM) is one of the most commonly used analysis tools of the semiconductor industry today. But the applications of the SEM on modern ULSI circuit technology have met limitations due to their resolution maximum which is about 12 angstroms. In order to clearly find the tiny features of modern semiconductor devices, a transmission electron microscope (TEM) is used because of its high resolution which is up to 1.4 angstroms. However, the TEM analysis still cannot be available in some situations, where for example, the sample being analyzed has photoresist material, and more particularly as a patterned photoresist layer of a sample itself is the main object being observed. Using a TEM to analyze a patterned photoresist layer having tiny features overcomes a problem resulting from the sample preparation process comprising a slicing process, a grinding process, a polishing process and a cleaning process. Furthermore, the slicing process using a focused ion beam (FIB) definitely causes damage to the photoresist layer and breaks the characteristics. Moreover, the cleaning process using an organic solvent to clean the sample renders the TEM analysis on a photoresist layer impractical since the organic solvent such as acetone will completely destroy the features.

Another problem of a TEM analysis on a photoresist layer results from the dimension distortion of the photoresist layer which appears in moisture and oxygen-contained environments. The dimension distortion of a patterned photoresist layer being observed will make the efforts of further process technology development uncertain since the true dimension of the defined pattern used to form tiny contact or via holes or gate electrodes is crucial as the line width or the technology level of the integrated circuit of the next generation advances further. Furthermore, still another problem of a TEM analysis on a photoresist layer results from the electron beams used to form images of the TEM since the electron beam bombardment which effectively acts as a heat source causes the photoresist layer to shrink.

Therefore, it is necessary to provide a novel TEM sample preparation technology to solve the problems mentioned above.

SUMMARY OF THE INVENTION

It is therefore an object of the invention to provide an analyzable photoresist sample for transmission electron microscope (TEM) analysis.

It is another object of this invention to provide a method of a TEM photoresist sample preparation without the charging problem and FIB slicing damage.

It is a further object of this invention to provide a TEM photoresist sample having a true dimension and render the clear profile observation and the precise dimension measurement of a defined photoresist layer used to define a deep submicron semiconductor device practical.

To achieve these objects, and in accordance with the purpose of the invention, the invention uses a conductive layer and a dielectric layer to protect a photoresist layer of a TEM sample. Both the conductive layer and the dielectric layer are formed by a physical vapor deposition process at a temperature in which the photoresist layer remains stable. During the sample slicing and the TEM observation process, the dimension of the patterned photoresist layer could be maintained. Thus the clear profile observation and the precise dimension measurement of the patterned photoresist layer will be practical.

It is to be understood that both the foregoing general description and the following detailed description are exemplary and explanatory only and are not restrictive of the invention, as claimed.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

It is to be understood and appreciated that the process steps and structures described below do not cover a complete process flow. The present invention can be practiced in conjunction with various integrated circuit fabrication techniques that are used in the art, and only so much of the commonly practiced process steps are included herein as are necessary to provide an understanding of the present invention.

The present invention will be described in detail with reference to the accompanying drawings. It should be noted that the drawings are in greatly simplified form and they are not drawn to scale. Moreover, dimensions have been exaggerated in order to provide a clear illustration and understanding of the present invention.

Figure 1:
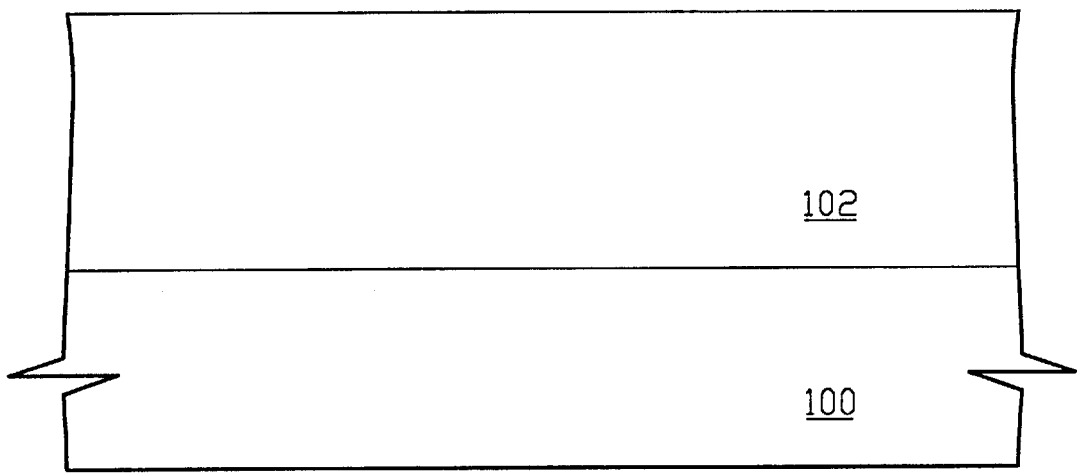
FIG. 1 shows a cross-sectional view of a substrate having a photoresist layer thereon.

Referring to FIG. 1, a substrate 100 having a photoresist layer 102 thereon is shown. The substrate 100 can be a semiconductor substrate, such as a silicon wafer, but it is not necessarily a semiconductor substrate. The substrate 100 can also comprise either a dielectric layer or a conductive layer thereon. In fact, the substrate 100 depends on the need of analysis. The photoresist layer 102 can be any photoresist material used in modern semiconductor industry. Moreover, the photoresist layer 102 can be formed over the substrate 100 via conventional methods in the art, for example, a spin coating method.

Figure 2A:
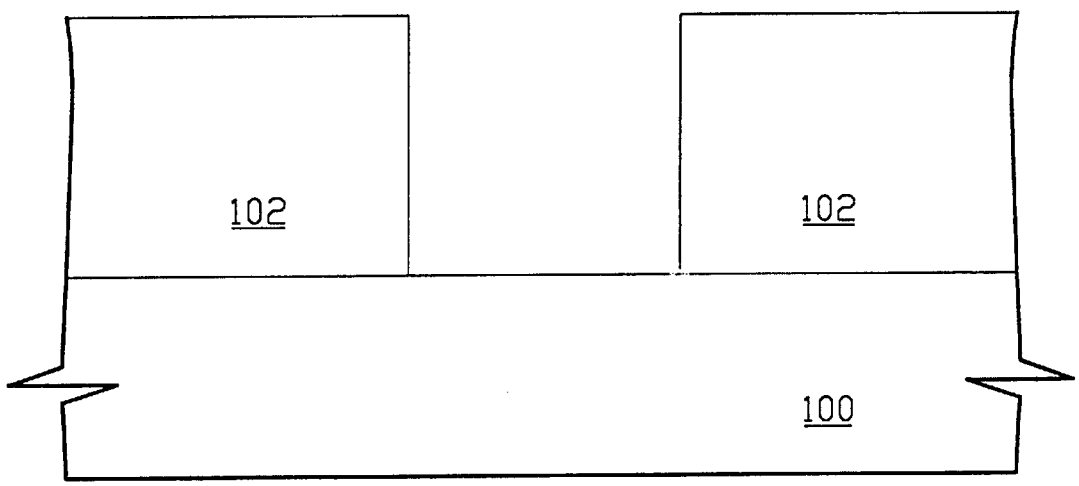
FIG. 2A shows a hole formed in the photoresist layer shown in FIG. 1.
Figure 2B:
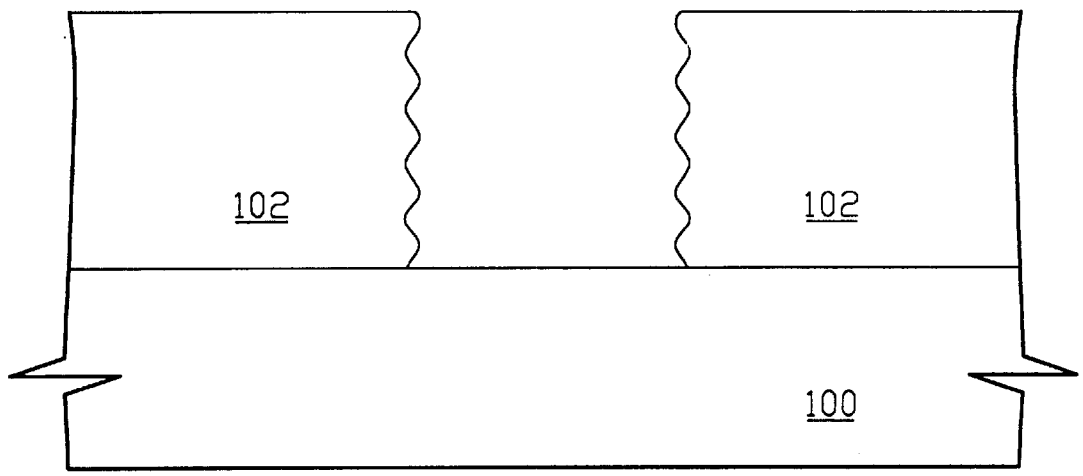
FIG. 2B shows a profile of the hole resulting from the standing wave effect.

Referring to FIG. 2A, in order to find the profile of a developed photoresist layer in the formation of a contact hole or a via hole, a hole pattern is transferred into the photoresist layer 102 to expose the substrate 100 by a conventional photolithography process. After developing the photoresist layer 102, the hole is formed. More particularly, owing to the standing wave effect, the sidewall of the hole has a profile shown in FIG. 2B. The profile can only be found via a TEM analysis having a resolution of about 1.4 angstroms to about 1.8 angstroms because the dimensions of the caves of the profile is tiny if the width of the hole shown in FIG. 2B is less than about 0.2 micron. It is apparent that the profile is crucial if one needs to measure the width of the hole precisely.

Figure 3:
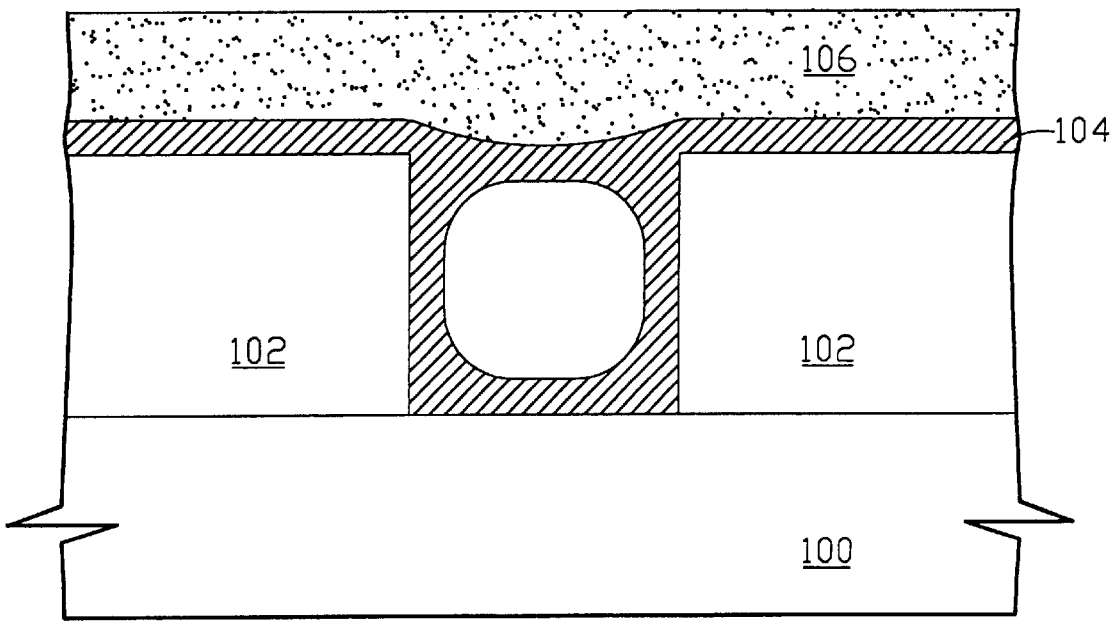
FIG. 3 shows a result of sequentially forming a conductive layer and a dielectric layer on the structure shown in FIG. 2A.

Referring to FIG. 3, a conductive layer 104 is formed over the photoresist layer 102 and the bottom of the hole shown in FIG. 2A and a dielectric layer 106 is sequentially formed thereon. The conductive layer 104 can be a platinum layer, a gold layer, a copper layer, an aluminum layer or a titanium layer, although it is preferably a platinum layer. Platinum is chosen because it is a kind of stable or noble metal and it can be formed with a very thin thickness. The conductive layer 104 is preferably formed via a physical vapor deposition (PVD) process, for example, a DC sputtering process performed at about 20° C. to about 30° C. The temperature of the PVD process is necessarily low because a high temperature environment would cause the photoresist material to shrink or change shape. In fact, not only is it that the formation temperature of the conductive layer cannot be over a certain temperature at which the photoresist layer starts to shrink or change its shape, but also the temperature of the entire TEM photoresist sample preparation process cannot exceed the certain temperature. The thickness of the conductive layer 104 is between about 50 to about 200 angstroms, and is preferably about 100 angstroms. As shown in FIG. 3, the conductive layer 104 fails to fill the hole due to the tiny dimension of the hole and the limited step coverage ability of the PVD process. However, this profile is not crucial for this invention. The conductive layer 104 is used to isolate the photoresist layer 102 from moisture environment and insulates the photoresist layer 102 from oxidation. Furthermore, the conductive layer 104 can also avoid the charging effect resulting from the use of electron or ion beams. Moreover, the conductive layer 104 is very helpful to clarify the interface between the photoresist layer 102 and the dielectric layer 106. The dielectric layer 106 can be either a silicon dioxide layer or a silicon nitride layer, and is preferably a silicon dioxide layer. The dielectric layer 106 is formed via a physical vapor deposition process, and preferably a DC sputtering process. The sputtering process is performed via an ion miller used in the conventional TEM sample preparation. By accelerating argon ion ($Ar^+$) plasma, silicon dioxide or silicon nitride molecules are sputtered from a quartz glass target or a silicon nitride target. The sputtering process is performed at a pressure of about $10^{-6}$ torr. This sputtering process is also performed at about 20° C. to about 30° C. The thickness of the dielectric layer 106 is between about 500 angstroms to about 1 micron, and is preferably 1000 angstroms. The dielectric layer 106 is used to protect the photoresist layer 102 from being damaged amid the sample slicing process by a focused ion beam (FIB) technique using gallium ions ($Ga^+$). It is found that the damage thickness of a common focused ion beam slicing is about 500 angstroms. The thickness of the protective dielectric layer must exceed 500 angstroms.

Figure 4:
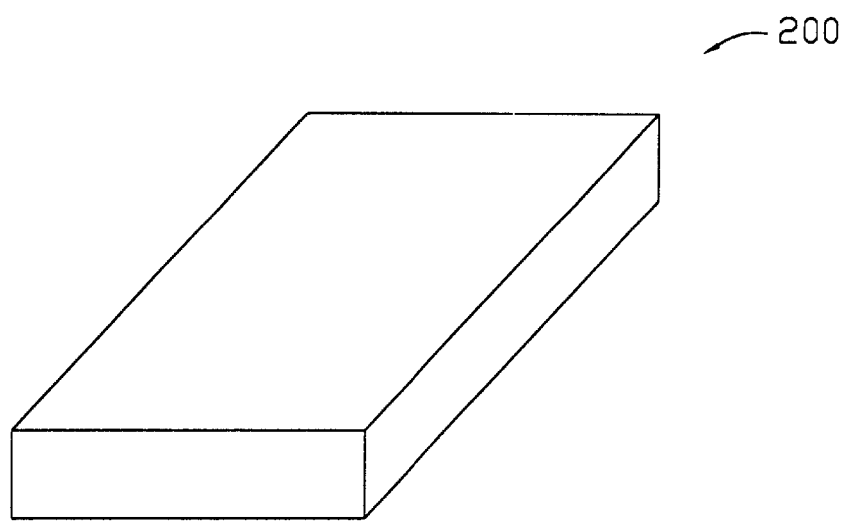
FIG. 4 shows a TEM sample prepared by the method of the present invention.

After forming the dielectric layer 102, the substrate 100 such as a silicon wafer is sliced by using a FIB to form TEM samples 200 having dimensions of about 10 microns × about 5 microns × about 0.2 micron as shown in FIG. 4, wherein the length is about 10 microns, the width is about 5 microns and the thickness is about 0.2 micron. In order to observe the TEM sample prepared by the method of the invention, the TEM sample 200 is then placed on a copper net having a carbon film coated thereon via an electrostatic pick up method using a glass needle having a tiny tip of about 1 micron.

Figure 5:
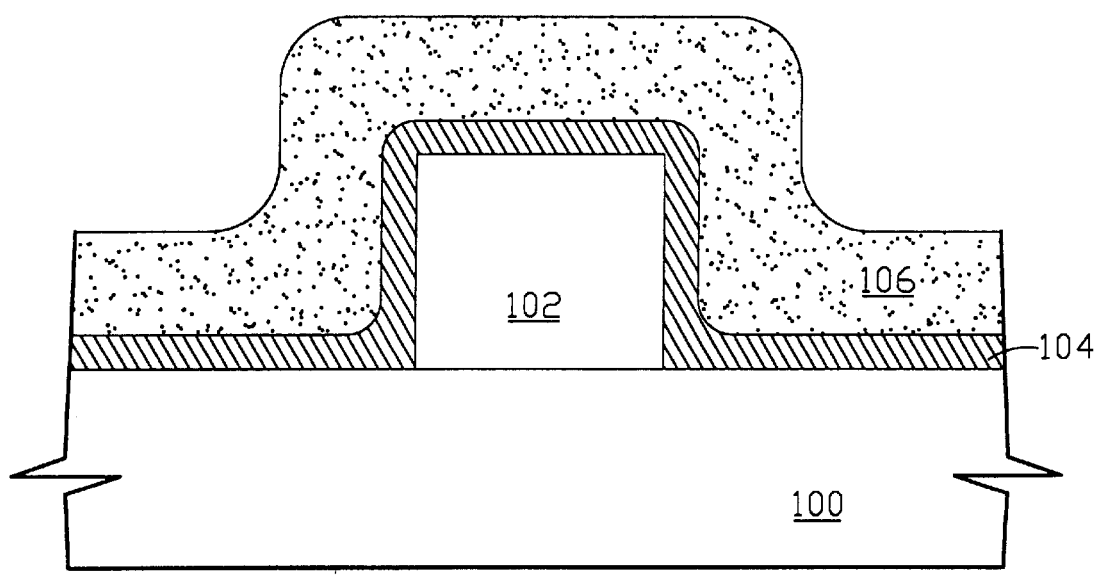
FIG. 5 shows another application of the invention on researching the profile of a photoresist layer defining a gate electrode.

The method of the TEM sample preparation set forth is used to prepare a photoresist sample having via or contact holes therein. However, this method can also be used to prepare a photoresist sample having other structures. For example, as shown in FIG. 5, the photoresist layer 102 is used to define a gate electrode and the substrate 100 can be a conductive layer such as a polysilicon layer. In every embodiment of this invention, the conductive layer 104 and the dielectric layer 106 can protect the photoresist layer 102 and isolate the photoresist layer 102 from a moisture and oxygen-containing environment. Moreover, the contraction of the photoresist layer 102 amid the bombardments by electron beams of a TEM or a FIB will be avoided effectively. The conductive layer 104 is mainly used to release the charges resulting from the electron beams of a TEM or a FIB. Because the sample 200 observed is placed on a carbon film on a copper net, the conductive layer 104 may be omitted.

Other embodiments of the invention will appear to those skilled in the art from consideration of the specification and practice of the invention disclosed herein. It is intended that the specification and examples to be considered as exemplary only, with the true scope and spirit of the invention being indicated by the following claims.

What is claim is:

1. A method of sample preparation for transmission electron microscope analysis, said method comprising:

providing a substrate having a photoresist layer thereon;

forming a dielectric layer over said substrate; and slicing said substrate.

2. The method according to claim 1, wherein said substrate comprises a silicon wafer.

3. The method according to claim 1, wherein said substrate comprises a conductive layer.

4. The method according to claim 1, wherein said substrate comprises a dielectric layer.

5. The method according to claim 1, wherein said dielectric layer comprises a silicon dioxide layer.

6. The method according to claim 1, wherein dielectric layer comprises a silicon nitride layer.

7. The method according to claim 1, wherein said dielectric layer is formed by a physical vapor deposition process.

8. The method according to claim 1, wherein said dielectric layer is preferably formed at a temperture of about 20° C. to about 30° C.

9. The method according to claim 1, wherein said substrate is sliced via a focused ion beam.

10. A method of sample preparation for transmission electron microscope analysis, said method comprising:

providing a substrate having a photoresist layer thereon;

forming a conductive layer over said substrate by a first physical vapor deposition process;

forming a dielectric layer over said conductive layer by a second physical vapor deposition process; and slicing said substrate.

11. The method according to claim 10, wherein said substrate comprises a silicon wafer.

12. The method according to claim 10, wherein said substrate comprises a conductive layer.

13. The method according to claim 10, wherein said substrate comprises a dielectric layer.

14. The method according to claim 10, wherein said conductive layer comprises a platinum layer.

15. The method according to claim 10, wherein said conductive layer comprises a copper layer.

16. The method according to claim 10, wherein conductive layer comprises a gold layer.

17. The method according to claim 10, wherein said conductive layer comprises an aluminum layer.

18. The method according to claim 10, wherein said dielectric layer comprises a silicon dioxide layer.

19. The method according to claim 10, wherein dielectric layer comprises a silicon nitride layer.

20. The method according to claim 10, wherein said first physical vapor deposition process comprises a sputtering process.

21. The method according to claim 10, wherein said second physical vapor deposition process comprises a sputtering process.

22. The method according to claim 10, wherein said first and said second physical deposition processes are preferably performed at a temperature of about 20° C. to about 30° C.

23. The method according to claim 10, wherein said substrate is sliced via a focused ion beam.

24. A method of sample preparation for transmission electron microscope analysis, said method comprising:

providing a substrate having a photoresist layer thereon;

forming a conductive layer over said substrate by a first sputtering deposition process;

forming a dielectric layer over said conductive layer by a second sputtering deposition process; and slicing said substrate.

25. The method according to claim 24, wherein said substrate comprises a silicon wafer.

26. The method according to claim 24, wherein said substrate comprises a conductive layer.

27. The method according to claim 24, wherein said substrate comprises a dielectric layer.

28. The method according to claim 24, wherein said conductive layer comprises a platinum layer.

29. The method according to claim 24, wherein said conductive layer comprises a copper layer.

30. The method according to claim 24, wherein conductive layer comprises a gold layer.

31. The method according to claim 24, wherein said conductive layer comprises an aluminum layer.

32. The method according to claim 24, wherein said dielectric layer comprises a silicon dioxide layer.

33. The method according to claim 24, wherein dielectric layer comprises a silicon nitride layer.

34. The method according to claim 24, wherein said first and said second sputtering deposition processes are preferably performed at a temperature of about 20° C. to about 30° C.

35. The method according to claim 24, wherein said substrate is sliced via a focused ion beam.

* * * * *